US00PP20299P2

(12) United States Plant Patent
Bremner

(10) Patent No.: US PP20,299 P2
(45) Date of Patent: Sep. 15, 2009

(54) ***POTENTILLA* PLANT NAMED 'SETTING SUN'**

(50) Latin Name: *Potentilla fruticosa*
Varietal Denomination: SETTING SUN

(76) Inventor: Alan Heddle Bremner, Bendigo St. Ola, Kirkwall, Orkney (GB), KW15 1SX ( * ) Notice: Subject to any disclaimer, the term of this patent is extended or adjusted under 35 U.S.C. 154(b) by 8 days.

(21) Appl. No.: 12/154,201

(22) Filed: May 19, 2008

Related U.S. Application Data

(60) Provisional application No. 60/932,264, filed on May 29, 2007.

(51) Int. Cl.
*A01H 5/00* (2006.01)

(52) U.S. Cl. ..... Plt./237

(58) Field of Classification Search ..... Plt./237
See application file for complete search history.

*Primary Examiner*—June Hwu

(57) ABSTRACT

A new cultivar of *Potentilla* plant named 'Setting Sun' that is characterized by compact habit, dense grey-green foliage, and unusual peach colored flowers which bear a darker peach-red eye. In combination these traits set 'Setting Sun' apart from all other varieties of *Potentilla* known to the inventor.

2 Drawing Sheets

Genus: *Potentilla.*
Species: *fruticosa.*
Denomination: 'Setting Sun'.

BACKGROUND OF THE INVENTION

The present invention relates to a new and distinct cultivar of *Potentilla,* commonly known as Bush Cinquefoil, or Shrubby *Potentilla,* which is grown as a dwarf summer-flowering shrub for use in the garden and landscape. The new cultivar is known botanically as *Potentilla fruticosa,* and will be referred to hereinafter by the cultivar name 'Setting Sun'. 'Setting Sun' arose from a breeding program carried out by the inventor at the inventor's nursery on the Island of Orkney in Scotland, United Kingdom, which the inventor commenced in 1976.

Shrubby *Potentillas* are especially well-adapted to the harsh weather conditions of Orkney which experiences long, dull and wet winters, with salt-laden winds and frequent severe gales. Settings are short and cool, and the prevailing soil type is heavy boulder clay. Although *Potentillas* suffer die-back in these conditions, re-growth occurs quickly and flowering occurs and persists during the summer and early autumn months.

Initially, the inventor gathered together approximately sixty named cultivars of *Potentilla,* and planted them in the open ground with the intention of facilitating open pollination. Seed was harvested each autumn and seedlings raised the following spring. As the inventor observed the flowering and plant habit of each new seedling, it was either discarded or re-planted in association with similar selections in order to encourage open pollination within each color group. The initial aim of the breeding program was to produce robust white-flowered forms. More recently the inventor has been interested in producing a collection of new *Potentilla* varieties with novel flower colors and improved plant habit leading to better garden and landscape performance.

'Setting Sun' was identified and selected in 1989 for its combination of unusual peach colored flowers which bear a darker peach-red eye. The inventor is not aware of any other varieties of *Potentilla* which exhibit such a flower color combination. 'Setting Sun' was also selected for its compact habit which is retained without the need for pruning.

The male and female parents of 'Setting Sun' were unnamed and unreleased seedlings which the inventor had raised from previous open pollinations going back to the inventor's original acquisition of named cultivars.

'Setting Sun' was first asexually propagated by the inventor in Orkney, Scotland, United Kingdom in summer 1989, by taking softwood cuttings. The plants resulting from this first and from all subsequent generations have grown and flowered uniformly and identically with the inventor's initial selection. The inventor has determined that the new variety 'Setting Sun' is stable and reproduces true to type in successive generations of asexual propagation.

SUMMARY OF THE INVENTION

The following traits have been repeatedly observed and represent the distinguishing characteristics of the new *Potentilla* cultivar named 'Setting Sun'. These traits in combination distinguish 'Setting Sun' from all other varieties of *Potentilla* known to the inventor. The new invention has not been tested under all possible conditions and phenotypic differences may be observed with variations in environmental, climatic, and cultural conditions, however, without any variance in genotype.

1. 'Setting Sun' is a compact upright bush which at maturity attains a height of 70 cm and spread of 1 meter without pruning.
2. After three years of growing out of doors in a container, 'Setting Sun' reaches 50 cm. in height and 30 cm. in width.
3. 'Setting Sun' exhibits dense grey-green foliage.
4. The flowers of 'Setting Sun' are peach in color, bearing a darker peach-red eye.
5. 'Setting Sun' grows well in moist well-drained soils in full sun to partial shade.
6. 'Setting Sun' is hardy to USDA Zone 3.

BRIEF DESCRIPTION OF THE DRAWINGS

The accompanying color drawings illustrate the overall appearance of the new *Potentilla* variety named 'Setting Sun' showing color as true as is reasonably possible to obtain in color reproductions of this type. The plant depicted in the drawings is 3-years-old and growing out-of-doors in Arroyo Grande, Calif.

Drawing labeled

Drawing labeled

Figure 1:
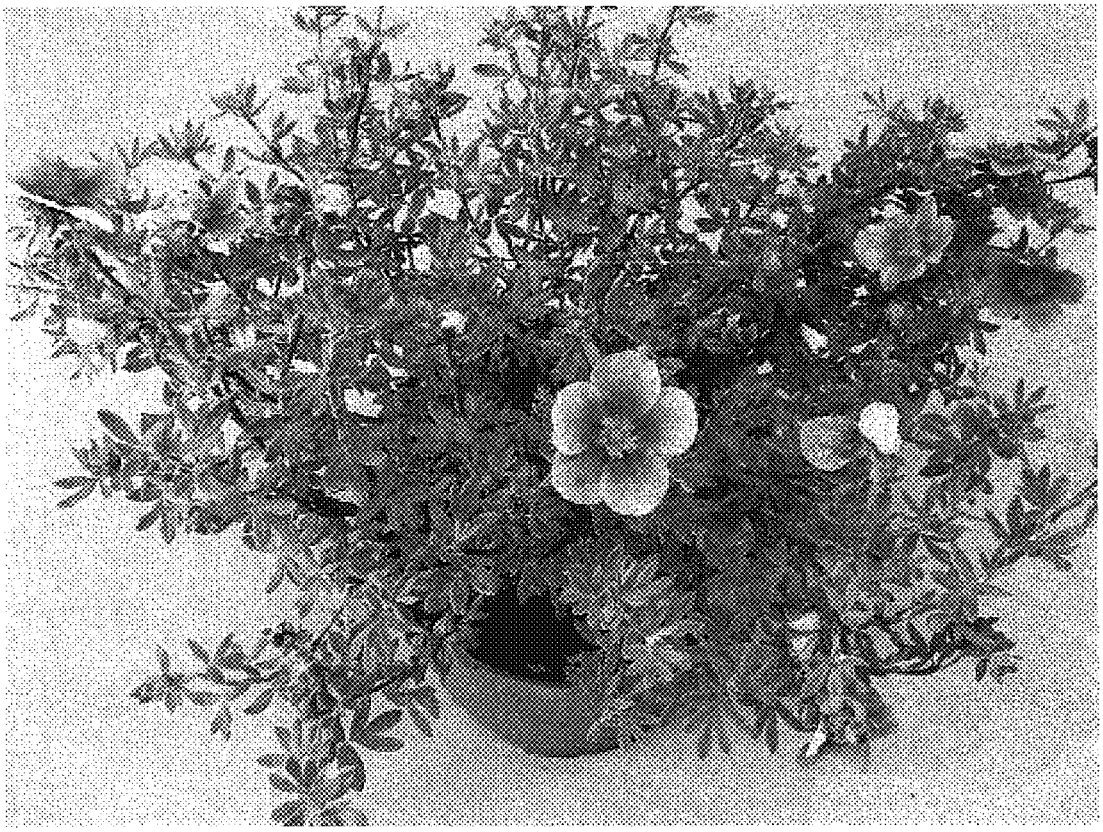
FIG. 1 depicts 'Setting Sun' in bloom.
Figure 2:
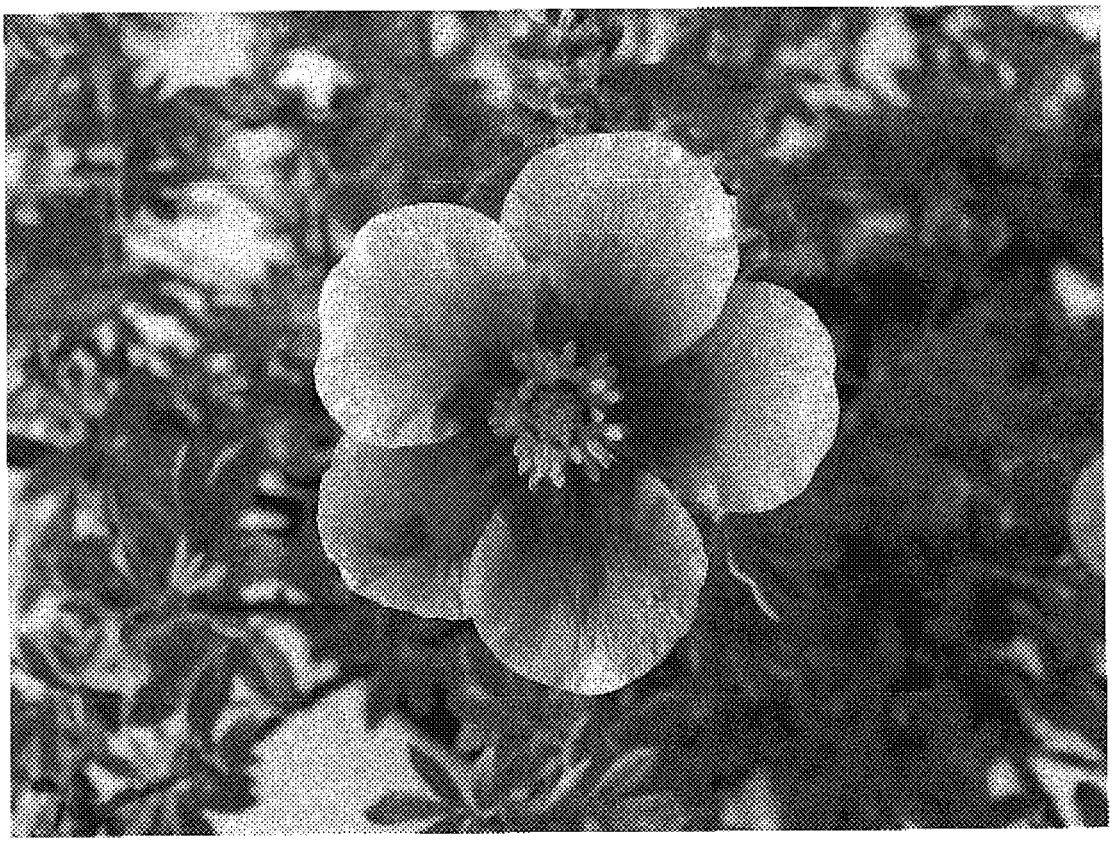
FIG. 2 depicts a close-up view of the flower.

Color in drawings may differ from color values cited in the detailed botanical description, which accurately describe the actual color of the new variety 'Setting Sun'. Drawings were made using conventional techniques and although color may appear different from actual color due to light reflectance, they are as accurate as possible by conventional photography.

BOTANICAL DESCRIPTION OF THE PLANT

The following is a detailed description of the new *Potentilla* cultivar named 'Setting Sun'. Data was collected in Arroyo Grande, Calif. from 3-year-old plants growing out-of-doors. Color determinations are in accordance with The 2001 Royal Horticultural Society Colour chart except where general color terms of ordinary dictionary significance are used. The growing requirements are similar to the species and no disease problems have been observed.

Botanical classification: *Potentilla fruticosa* 'Setting Sun'.
Family: Rosaceae.
Genus: *Potentilla.*
Species: *fruticosa.*
Denomination: 'Setting Sun'.
Common name: Cinequefoil.
Parentage: 'Setting Sun' is a hybrid plant that resulted from open pollination of unnamed and unreleased open pollinated seedlings. The male and female parents are unknown.
Type: Deciduous shrub.
Use: For use in border and landscape.
Commercial classification: Sub-shrub.
Vigor: Low.
Root system: Fine and fibrous.
Habit: Upright.
Height (*at maturity*).—70 cm.
Width (*at maturity*).—1 m.
Height after 3 years: 50 cm.
Width after 3 years: 30 cm.
Hardiness: USDA Zone 3.
Seasonal interest: Profuse flowering in spring and summer.
Propagation method: Stem cuttings.
Cultural conditions: Grow in full sun and well-draining soil, with moderate water.
Crop time (range): 9–12 months are needed to produce a finished 1-liter container from a rooted cutting.
Rooting time (average): 6–8 weeks are needed for an initial cutting to produce roots.
Susceptibility to pests and disease: No susceptibility to pests or disease known to the inventor.
Stem:
- *Branching.*—Dense lateral branching.
- *Main trunk color.*—165A.
- *Trunk surface.*—Scurfy.
- *Trunk width.*—4 cm.
- *Stem shape.*—Subcylindrical.
- *Stem color.*—183A and 178A both present.
- *Stem surface.*—Villous.
- *Stem dimensions* (*range*).—18 cm–23 cm. in length and 2 mm. in diameter.
- *Internode* (*range*).—1.50 cm–2 cm.

Foliage:
- *Type.*—Winter deciduous.
- *Leaf arrangement.*—Alternate.
- *Leaf division.*—Palmate.
- *Leaf dimensions* (*range*).—1.25 cm–2.75 cm. in length and 1.50 cm–3 cm. in width.
- *Leaf color* (*abaxial surface*).—N138D.
- *Leaf color* (*adaxial surface*).—In the range N138A to N138B.
- *Leaf shape.*—Flabellate.
- *Leaf attachment.*—Petiolate.
- *Petiole shape.*—Cylindrical.
- *Petiole color.*—N138D.
- *Petiole surface.*—Pubescent.
- *Petiole dimensions.*—1.50 cm. in length and 1 mm. in width.
- *Leaf margin.*—Divided.
- *Leaflets* (*range*).—3–5 in number.
- *Leaflet dimensions* (*range*).—1.0 cm–1.50 cm. in length and 0.40–0.60 cm. in width.
- *Leaflet surface* (*abaxial and adaxial*).—Pubescent.
- *Leaflet shape.*—Spatulate.
- *Leaflet apex.*—Rounded.
- *Leaflet base.*—Attenuate.
- *Leaf venation.*—Reticulate.
- *Vein color* (*abaxial surface*).—N138D.
- *Vein color* (*adaxial surface*).—N138D.
- *Foliar fragrance.*—None observed.

Flower:
- *Inflorescence.*—Solitary.
- *Flower arrangement.*—Terminal.
- *Flower quantity* (*range*).—50–80 on an individual plant.
- *Flower shape.*—Saucer-shaped.
- *Flower dimensions.*—1 cm. in depth and 3.70 cm. in diameter.
- *Aspect.*—Facing upward and outward.
- *Self-cleaning or persistent.*—Self-cleaning.
- *Flower color.*—39A, 26C and 26B are all present.
- *Petals.*—5 in number.
- *Petal dimensions.*—1.50 cm. in length and 1.50 cm. in width.
- *Petals fused or unfused.*—Unfused.
- *Petal margin.*—Entire.
- *Petal apex.*—Obtuse.
- *Petal base.*—Truncate.
- *Petal shape.*—Orbicular.
- *Petal surface* (*abaxial and adaxial*).—Glabrous.
- *Petal color* (*both surfaces*).—39A (base of petal), 26C and 26B are all present.
- *Bud color.*—179A.
- *Bud shape.*—Obovate.
- *Bud surface.*—Puberulent.
- *Bud dimensions.*—4 mm. in height and 5 mm. in width.
- *Bud quantity* (*range*).—50–80 on an individual plant.
- *Sepals.*—5 in number.
- *Sepals fused or unfused.*—Unfused.
- *Sepal margin.*—Entire.
- *Sepal apex.*—Apiculate.
- *Sepal surface* (*abaxial*).—Villous.
- *Sepal surface* (*adaxial*).—Puberulent.

*Sepal color* (*abaxial and adaxial surfaces*).—182A and 153B are both present.

*Sepal dimensions.*—6 mm. in length and 5 mm. in width.

*Bractlets.*—5 subtending sepals.

*Bractlets fused or unfused.*—Unfused.

*Bractlet margin.*—Entire.

*Bractlet apex.*—Apiculate.

*Bractlet surface* (*abaxial*).—Villous.

*Bractlet surface* (*adaxial*).—Puberulent.

*Bractlet color* (*abaxial and adaxial surfaces*).—137B.

*Bractlet dimensions.*—6 mm. in length and 5 mm. in width.

*Calyx dimensions.*—1 cm. in diameter.

*Calyx surface* (*abaxial surface*).—Villous.

*Calyx surface* (*adaxial surface*).—Puberulent.

*Calyx shape.*—Stellate.

*Calyx color.*—182A, 153B and 137B are all present.

*Peduncle shape.*—Cylindrical.

*Peduncle surface.*—Villous.

*Peduncle color.*—N144C.

*Peduncle dimensions.*—0.75 cm. in length and less than 1 mm. in diameter.

*Flower fragrance.*—Delicate sweet scent.

Reproductive organs:

*Stamens.*—About 20.

*Stamen color.*—153B.

*Stamen length.*—2 mm.

*Carpel.*—Less than 10.

*Carpel color.*—163C.

*Carpel length.*—Less than 1 mm.

*Pollen.*—Low amount.

*Pollen color.*—163C.

*Anther.*—About 20 in number.

*Anther shape.*—Hastate.

*Anther color.*—163C.

*Anther length.*—Less than 1 mm.

*Ovary position.*—Inferior.

*Ovary color.*—163D.

*Ovary shape.*—Convex.

*Ovary dimensions.*—1 mm. in height and 2 mm. in diameter.

Seed: None observed to date.

What is claimed is:

1. A new and distinct variety of *Potentilla* plant named 'Setting Sun' as described and illustrated herein.

* * * * *